(12) United States Patent
Jeong et al.

(10) Patent No.: US 8,656,788 B2
(45) Date of Patent: Feb. 25, 2014

(54) RING SHEAR APPARATUS CONSIDERING WALL-SLIP EFFECT

(71) Applicant: Korea Institute of Geoscience and Mineral Resources (KIGAM), Daejeon (KR)

(72) Inventors: Sueng-Won Jeong, Daejeon (KR); Young-Suk Song, Daejeon (KR); Choon Oh Lee, Daejeon (KR); Kyeong-Su Kim, Daejeon (KR)

(73) Assignee: Korea Institute of Geoscience and Mineral Resources (KIGAM), Daejeon (KR)

( * ) Notice: Subject to any disclaimer, the term of this patent is extended or adjusted under 35 U.S.C. 154(b) by 0 days.

(21) Appl. No.: 13/624,076

(22) Filed: Sep. 21, 2012

(65) Prior Publication Data

US 2013/0112013 A1    May 9, 2013

(30) Foreign Application Priority Data

Nov. 8, 2011    (KR) .......................... 10-2011-0116006

(51) Int. Cl.
  *G01N 3/32*    (2006.01)
(52) U.S. Cl.
  USPC ........................................ 73/815; 73/862.581
(58) Field of Classification Search
  USPC .............................. 73/760, 814–816, 862.581
  See application file for complete search history.

(56) References Cited

U.S. PATENT DOCUMENTS

| | | | | |
|---|---|---|---|---|
| 3,706,222 A * | 12/1972 | Smith et al. | ...................... | 73/809 |
| 3,709,031 A * | 1/1973 | Wilson et al. | ................... | 73/843 |
| 4,445,365 A * | 5/1984 | Selby | ........................... | 73/54.34 |
| 4,649,741 A * | 3/1987 | Strom | .............................. | 73/84 |
| 4,878,377 A * | 11/1989 | Abel | ............................ | 73/54.32 |
| 4,934,185 A * | 6/1990 | Nishiyama et al. | ......... | 73/150 A |
| 6,571,609 B1 * | 6/2003 | Bi | .............................. | 73/54.31 |

FOREIGN PATENT DOCUMENTS

| | | |
|---|---|---|
| JP | 05-034252 A | 2/1993 |
| JP | 10-206306 A | 8/1998 |
| JP | 11-064202 A | 3/1999 |
| JP | 2002-212938 A | 7/2002 |

\* cited by examiner

*Primary Examiner* — Max Noori
(74) *Attorney, Agent, or Firm* — Ladas & Parry LLP (57) ABSTRACT

A ring shear apparatus for measuring a shear strength of soil samples. The ring shear apparatus considering a wall-slip effect including: an upper ring for forming a first accommodation portion having a ring shape in which soil samples are accommodated; a lower ring for forming a second accommodation portion that corresponds to the first accommodation portion of the upper ring and has a ring shape in which soil samples are accommodated, closely attached to a lower portion of the upper ring and rotatably installed relative to the upper ring; a rotating unit for rotating the lower ring relative to the upper ring; and a shear strength measuring sensor combined with the upper ring and for measuring a shear strength of the soil samples, wherein a plurality of protrusions that protrudes from the lower ring is formed on an inner circumferential surface of the lower ring along a circumferential direction of the lower ring in order to prevent the soil samples from being slid when the lower ring is rotated.

12 Claims, 13 Drawing Sheets

RING SHEAR APPARATUS CONSIDERING WALL-SLIP EFFECT

CROSS-REFERENCE TO RELATED PATENT APPLICATION

This application claims the benefit of Korean Patent Application No. 10-2011-0116606, filed on Nov. 8, 2011, in the Korean Intellectual Property Office, the disclosure of which is incorporated herein in its entirety by reference.

BACKGROUND OF THE INVENTION

1. Field of the Invention

The present invention relates to a technology for reducing a natural disaster relating to a landslip, and more particularly, to a ring shear apparatus that may measure a shear strength that is a significant factor in evaluating the mobility of the landslip.

2. Description of the Related Art

Landslips take place when a soil mass slides along a thin soil layer above a bedrock due to external causes, such as an earthquake, isolated t-storms, thawing, and the like. Landslips in Korea usually take place due to isolated t-storms.

Slopes formed by landslips form action destructive surfaces gradually and undergo continuous sliding (slope action) and debris flow. For these reasons, the movement of a landslip is interpreted by dividing the landslip into (1) before destruction, (2) destruction, and (3) movement after destruction.

The soil mass in an area where a landslip takes place along the action destructive surfaces undergoes saturation and unsaturation repeatedly due to a change of rainfall and shows continuous strain. The stability of natural slopes is determined by strength characteristics (drainage and non-drainage shear strengths) as functions of time and strain. Shear strengths caused by strain before destruction are related to an early warning system for slopes and are essential parameters in evaluating the stability of slopes. The occurrence of the debris flow that corresponds to movement after destruction is directly related to a damage of infrastructure.

'A landslip that moves very slowly' corresponding to a stage before destruction proceeds at a speed of less than $10^{-6}$ cm/s. In this case, the soil mass on the natural slopes shows a progressive action, and it is difficult to identify movements of the slopes with naked eyes. The movement speed of the soil mass after the slopes reach destruction, is usually within a range of 0.1 cm/s. The movement of a landslip that moves faster than the movement speed of the soil mass within 0.1 cm/s is referred to as 'a landslip that moves very quickly', and the proceeding speed of the landslip that moves very quickly is generally 5 cm/s. In addition, when the soil loses its own soil strength, like liquefaction of sandy soil, due to the landslip, the debris flow occurs, and deposits move like a fluid, and the maximum movement speed of the deposits is 10 m/s.

Large and small landslips in Korea that take place due to annual isolated t-storms make living rights to be deteriorated, accompanied by social and economical losses over the living of people. In this way, the development of a test apparatus for predicting an unexpected landslip and evaluating the mobility of the debris flow that will occur after destruction is required. In particular, the development of a test apparatus that may perform quantitative measurement of a shear strength of the soil by varying a significant condition in a landslip, i.e., a saturation or unsaturation condition, a drainage or non-drainage condition, and a compaction or non-compaction condition, is needed.

Soil samples are accommodated in an upper ring and a lower ring of a general ring shear apparatus. A wall-slip effect that, when the upper ring and the lower ring are rotated relative to each other, the soil samples are slid on inner circumferential surfaces of the upper ring and the lower ring, occurs. If the soil samples are slid between the upper ring and the lower ring, a torque of the ring shear apparatus is decreased, and an error occurs when the shear strength of the soil is measured at the upper ring and the lower ring.

Thus, ring shear apparatuses that may measure a shear strength of the soil precisely by preventing soil samples from being slid on wall surfaces of an upper ring or a lower ring have to be developed.

SUMMARY OF THE INVENTION

The present invention provides a ring shear apparatus having improved precision of measurement in which a shear strength of soil that is a significant factor in predicting a landslip or evaluating the mobility of a debris flow caused by the landslip may be precisely measured by considering a wall-slip effect of soil samples.

According to an aspect of the present invention, there is provided a ring shear apparatus including: an upper ring for forming a first accommodation portion having a ring shape in which soil samples are accommodated; a lower ring for forming a second accommodation portion that corresponds to the first accommodation portion of the upper ring and that has a ring shape in which soil samples are accommodated, closely attached to a lower portion of the upper ring and rotatably installed relative to the upper ring; a rotating unit for rotating the lower ring relative to the upper ring; and a shear strength measuring sensor combined with the upper ring and for measuring a shear strength of the soil samples, wherein a plurality of protrusions that protrudes from the lower ring is formed on an inner circumferential surface of the lower ring along a circumferential direction of the lower ring in order to prevent the soil samples from being slid when the lower ring is rotated.

The ring shear apparatus may further include a core having a cylindrical shape and installed fixedly, wherein the upper ring is inserted in the core and is fixed to the core, and the first accommodation portion is formed by the upper ring and the core, and the lower ring is rotatably inserted in the core, and the second accommodation portion is formed by the lower ring and the core, and a plurality of protrusion that protrudes from the core is formed on an outer circumferential surface of the core along a circumferential direction of the core.

A plurality of protrusions that protrudes from may be formed on an inner circumferential surface of the upper ring along a circumferential direction of the upper ring.

The plurality of protrusions may have one cross-sectional shape selected from the group consisting of a semi-circular shape, a triangular shape, and a rectangular shape.

Convex portions may be formed on a support surface of the lower ring for supporting the soil samples and a top surface of the upper ring and are disposed in a radial shape.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

A ring shear apparatus considering a wall-slip effect (hereinafter referred to as a 'ring shear apparatus') according to an embodiment of the present invention will now be described more fully with reference to the accompanying drawings, in which exemplary embodiments of the invention are shown.

The ring shear apparatus according to the present invention is usually a test apparatus for providing basic data required for a warning system, such as prevention and measures for a landslip by evaluating slopes in a mountain district. In particular, the ring shear apparatus is to check a shear strength (shear resistance) of soil in a quantitative manner on various conditions, such as rainfall, gradient, drainage, saturation of an area (slope) where a landslip may take place.

Figure 1:
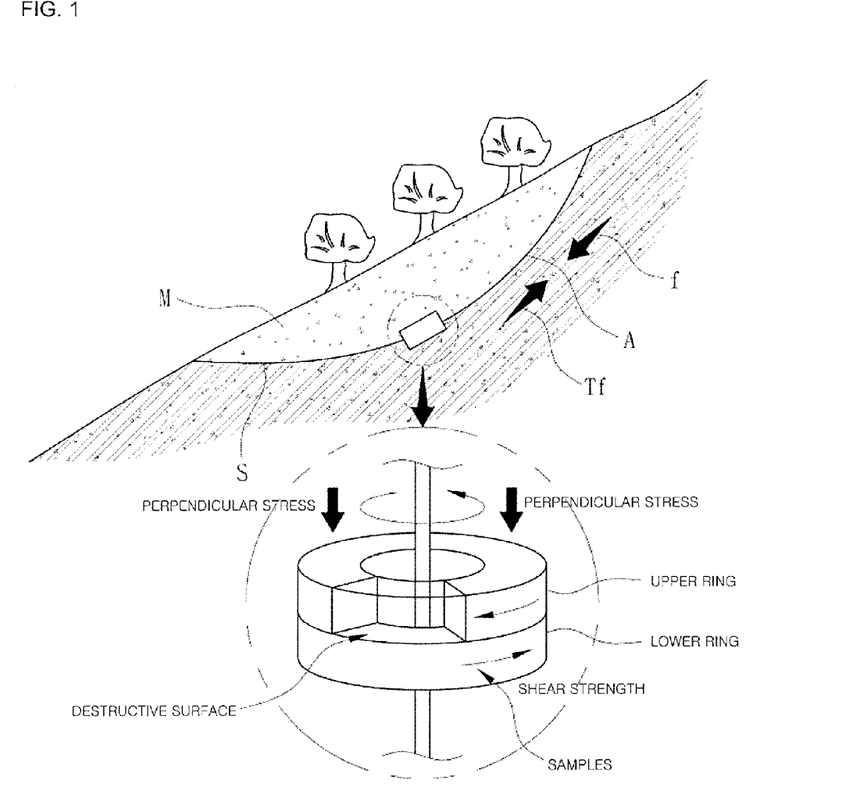
FIG. 1 is a schematic view of an object to be simulated of a ring shear apparatus according to an embodiment of the present invention.
Figure 2:
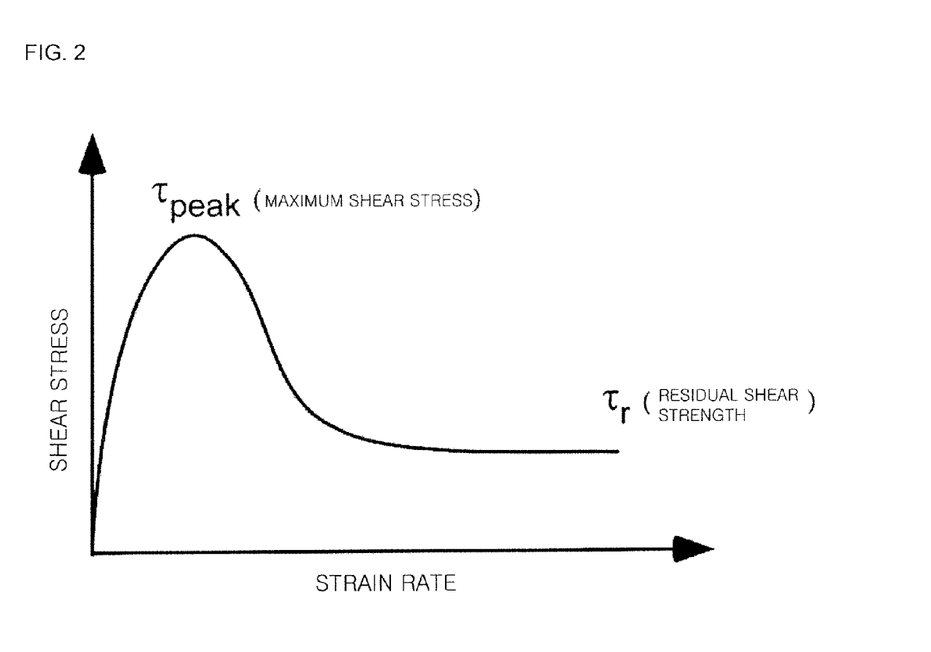
FIG. 2 is a graph showing the relationship between a shear strength of soil and a shear strain rate.

FIG. 1 is a schematic view of an object to be simulated of a ring shear apparatus according to an embodiment of the present invention, and FIG. 2 is a graph showing the relationship between a shear strength of soil and a shear strain rate.

The landslip generally takes place when a soil mass M slides along a boundary surface S (destructive surface) between a bedrock and a soil layer in a slope area. For example, at point A of FIG. 1, a shear resistance Tf (shear strength or shear stress) is generated in response to a stress f caused by gravity of the soil mass M at ordinary times so that balance of force is made at point A. When an intensive heavy rain takes place and rainwater flows into the soil mass M, displacement occurs, and balance of force is lost so that the soil mass M slides and a landslip takes place.

That is, referring to FIG. 2, when the soil mass M slides along the boundary surface S due to rainwater, or the like gradually, a shear stress is rapidly increased. When the amount of strain exceeds a peak point, the soil mass M does not resist any more, and destruction occurs in the boundary surface S.

According to the present invention, the above-described landslip procedure has been reproduced by using a test apparatus. That is, the ring shear apparatus according to the present invention has reproduced an area where a landslip takes place, by making an upper ring and a lower ring in which soil samples are accommodated, to be rotated relative to each other around the boundary surface (destructive surface). That is, the soil mass M in which the soil samples accommodated in the upper ring, the destructive surface (boundary surface) in which a boundary between the upper ring and the lower ring is destroyed, and the soil mass M (mainly, bedrock) in which the soil samples accommodated in the lower ring remain, have been reproduced.

In addition, a saturation or unsaturation condition, a drainage and non-drainage condition of the soil mass M, the size of a perpendicular stress, and a gradient of a slope, and the like are significant causes for a landslip. According to the present invention, the above conditions are reproduced similar to the reality by using various apparatuses in order to check the movement (in particular, shear strength) of the soil mass M during the landslip in a quantitative manner.

A specific structure of a ring shear apparatus according to an embodiment of the present invention will now be described in greater detail with reference to FIGS. 6 through 8.

Figure 6:
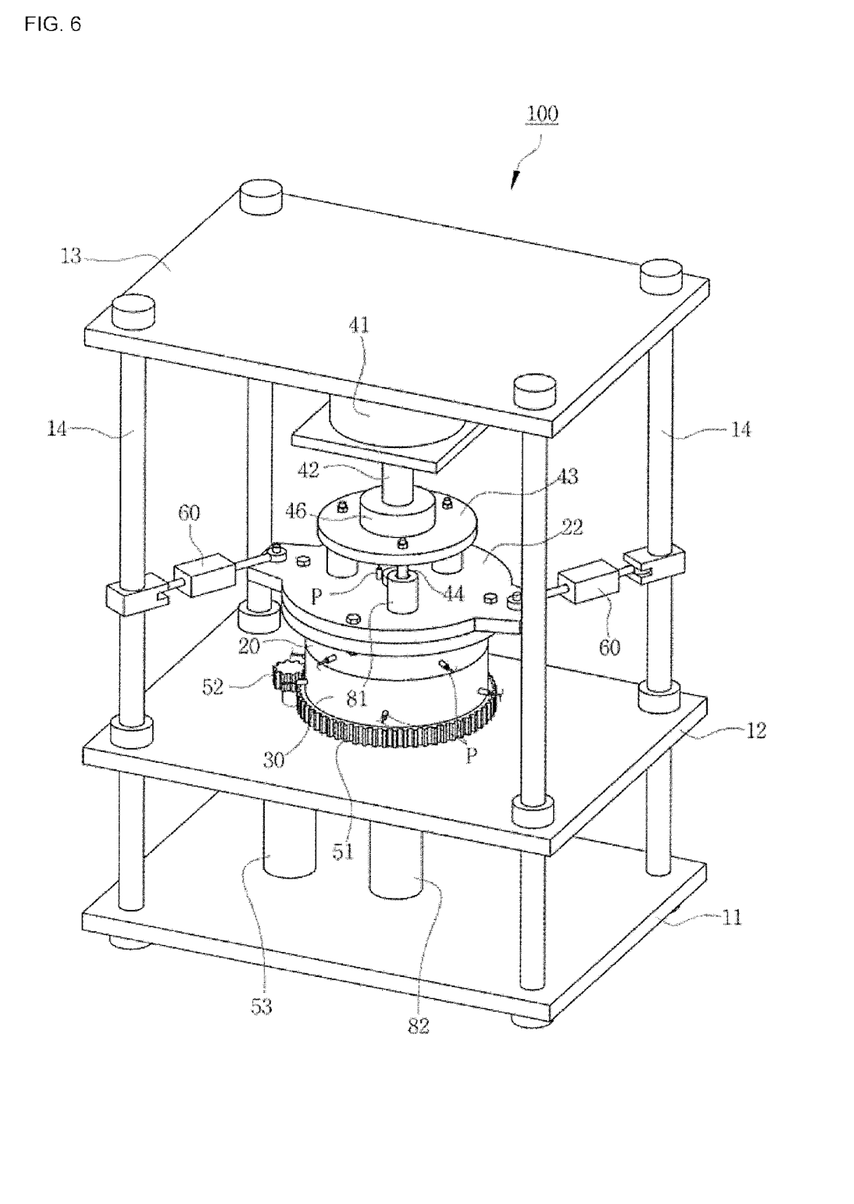
FIG. 6 is a schematic perspective view of a ring shear apparatus according to an embodiment of the present invention.
Figure 7:
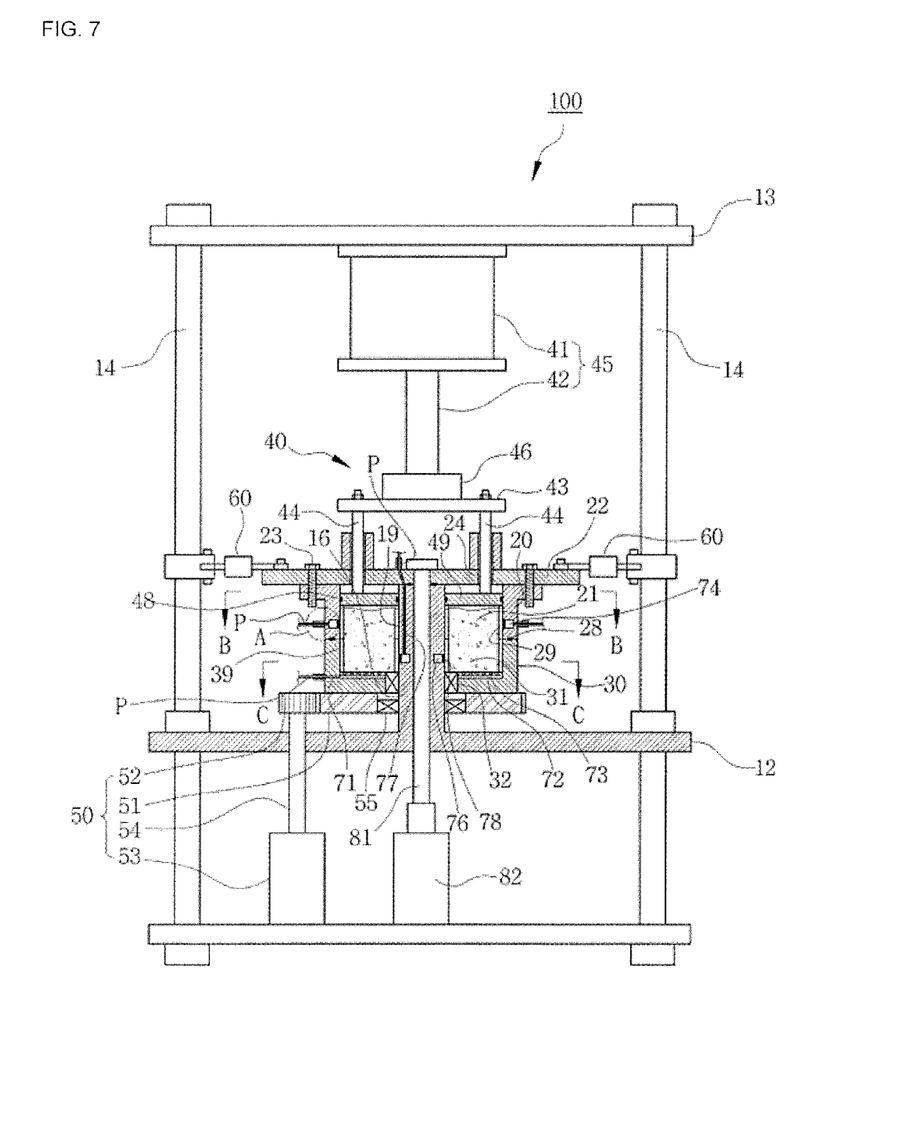
FIG. 7 is a schematic cross-sectional view of the ring shear apparatus illustrated in FIG. 6.
Figure 8:
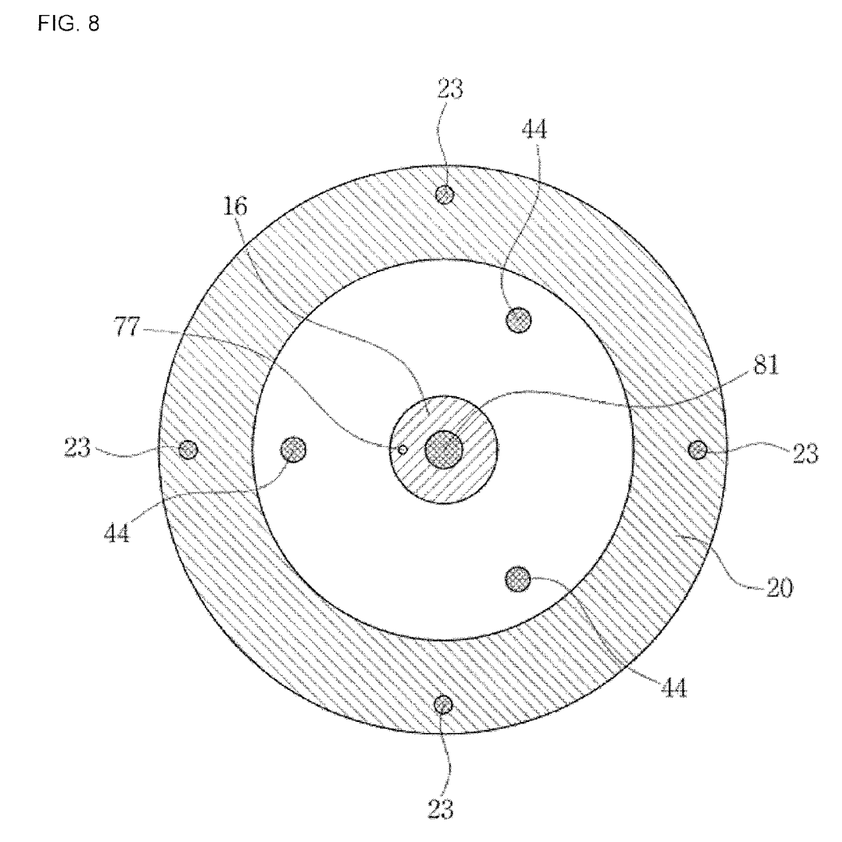
FIG. 8 is a schematic cross-sectional view taken along a line B-B of FIG. 7.

FIG. 6 is a schematic perspective view of a ring shear apparatus 100 illustrated in FIG. 1, FIG. 7 is a schematic cross-sectional view of the ring shear apparatus 100 illustrated in FIG. 6, and FIG. 8 is a schematic cross-sectional view taken along a line B-B of FIG. 7.

Referring to FIGS. 6 through 8, the ring shear apparatus 100 according to the current embodiment of the present invention includes a main body, an upper ring 20, a lower ring 30, a load applying unit 40, a rotating unit 50, and a shear strength measuring sensor 60.

The main body that supports elements, such as the upper ring 20 and the lower ring 30, and the like, which will be described later. The main body includes a base plate 11, a support plate 12, an upper plate 13, and a frame 14. The base plate 11, the support plate 12, and the upper plate 13 are disposed spaced apart from each other by a predetermined distance along a height direction, and the frame 14 connects the three plates 11, 12, and 13.

The upper ring 20 and the lower ring 30 are formed in ring shapes in order to reproduce a configuration in which a soil mass is destroyed along a destructive surface when a landslip takes place. That is, the lower ring 30 is exposed in an upward direction and includes a second accommodation portion 31 having a ring shape in which soil samples are accommodated, and the upper ring 20 is exposed in a downward direction and includes a first accommodation portion 21 having a ring shape in which the soil samples are accommodated.

A core 16 fixed onto the support plate 12 is disposed in the center of the upper ring 20 and the lower ring 30, respectively. In more detail, a core 16 having a cylindrical shape is disposed in the center of the upper ring 20 and the lower ring 30, respectively, so that the first accommodation portion 21 having a ring shape is formed between the upper ring 20 and the core 16 and the second accommodation portion 31 having a ring shape is formed between the lower ring 30 and the core 16. A bearing 32 is interposed between the lower ring 30 and the core 16 so that the lower ring 30 is rotatably supported.

Obviously, in another embodiment of the present invention, the upper ring 20 and the lower ring 30 themselves may form ring-shaped accommodation portions without using the core 16.

If the upper ring 20 is put on the lower ring 30 and is installed close to the lower ring 30, the first accommodation portion 21 of the upper ring 20 and the second accommodation portion 31 of the lower ring 30 correspond to each other and communicate with each other. Thus, the soil samples accommodated in the first accommodation portion 21 and the second accommodation portion 31 constitute a soil mass. A cover 22 is combined with an upper portion of the upper ring 20 via a screw 23, and the cover 22 closes the first accommodation portion 21 of the upper ring 20.

In addition, the upper ring 20 and the lower ring 30 are rotated relative to each other. They may be rotated in opposite directions, and only one thereof may be rotated, and the other one may stop. In the current embodiment, a configuration in which the lower ring 30 is rotated and the upper ring 20 stops, has been adopted.

In a general ring shear apparatus, a wall-slip effect that, when an upper ring and a lower ring are rotated relative to each other, as described above, soil samples slide on inner walls of the upper ring and the lower ring, occurs. For example, when the soil samples slide along wall surfaces, a shear strength of soil is not precisely transferred to the upper ring or the lower ring. Thus, a shear strength measuring sensor installed at the upper ring or the lower ring measures a value with a decreased torque so that reliability of measurement is lowered.

Figure 10:
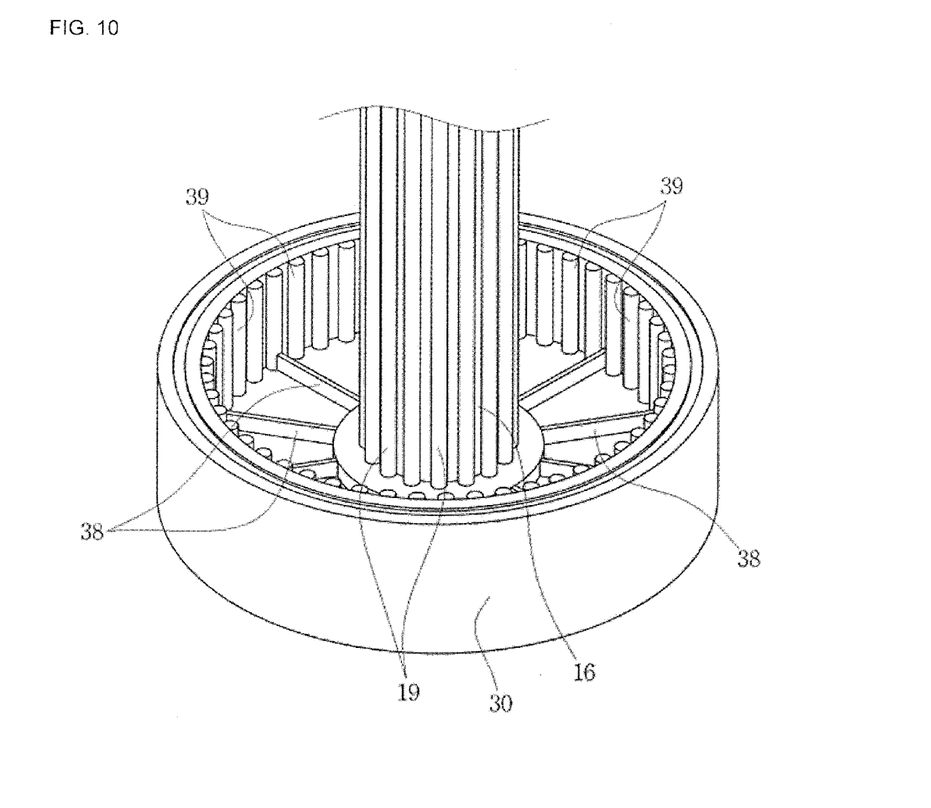
FIG. 10 is a schematic perspective view of a lower ring illustrated in FIG. 6.
Figure 11:
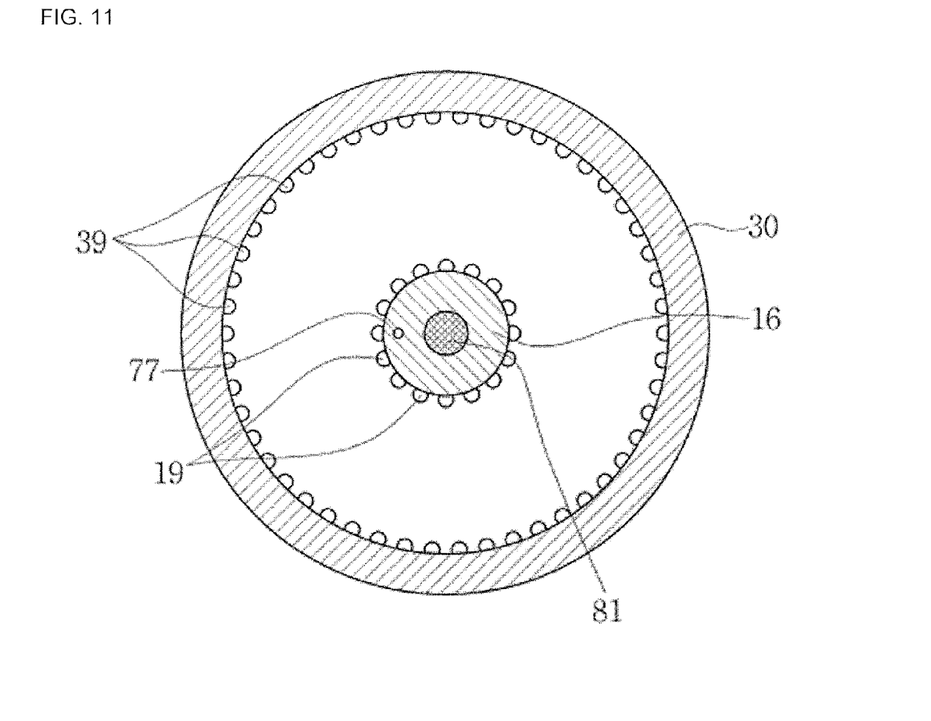
FIG. 11 is a schematic cross-sectional view taken along a line C-C of FIG. 7.

The problem has been solved by the present invention. A configuration considering a wall-slip effect according to the present invention will be described with reference to FIGS. 10 and 11. FIG. 10 is a schematic perspective view of the lower ring 30 illustrated in FIG. 6, and FIG. 11 is a schematic cross-sectional view taken along a line C-C of FIG. 7.

A plurality of protrusions 29, 39, and 19 are formed on inner circumferential surfaces of the upper ring 20 and the lower ring 30 and on an outer circumferential surface of the core 16 in order to consider a wall-slip effect that soil samples slid on wall surfaces of the upper ring 20 and the lower ring 30, respectively. The plurality of protrusions 19, 29, and 39 is used to form a wall surface of each of the upper ring 20 and the lower ring 30 as a rough surface.

Each of the protrusion 29, 39, and 19 protrudes from the wall surface, and the protrusions 29, 39, and 19 are spaced apart from each other by a predetermined distance along circumferential directions of the upper ring 20, the lower ring 30, and the core 16 and are consecutively disposed. In addition, each of the protrusions 29, 39, and 19 extends in a vertical direction to the height of the upper ring 20, the lower ring 30, and the core 16. Thus, the soil samples accommodated in the first accommodation portion 21 and the second accommodation portion 31 do not slide on the wall surfaces even though the upper ring 20 and the lower ring 30 are rotated relative to each other.

In the current embodiment, each of the protrusions 29, 39, and 19 protrudes from the wall surface to a height of about 3 mm or less, and a distance at which the protrusions 29, 39, and 19 are spaced apart from each other, is about 3 mm or less.

Thus, since the shear strength of the soil samples is not decreased and is transferred to the upper ring 20 or the lower ring 30, the shear strength measuring sensor 60 installed at the upper ring 20 or the lower ring 30 may measure the shear strength of soil precisely.

In addition, referring to FIG. 10, convex portions 38 are formed on a support surface of the lower ring 30. Here, the support surface is referred to as a surface on which the soil samples are put on the lower ring 30 and are supported. Although described later, in the current embodiment, a porous plate 73 is disposed spaced apart from a bottom surface of the lower ring 30 in an upward direction, and the porous plate 73 is a support surface for supporting the soil samples. The convex portions 38 formed on the support surface of the lower ring 30 are disposed in a radial shape from the center of the lower ring 30. The convex portions 38 are also formed on a top surface of the upper ring 20 that contacts the soil samples.

In this way, the convex portions 38 are formed on each of the top surface of the upper ring 20 and the support surface of the lower ring 30 so that the soil samples do not slide on upper and lower surfaces of the upper ring 20 and the lower ring 30 as well as on their inner circumferential surfaces.

Figure 12:
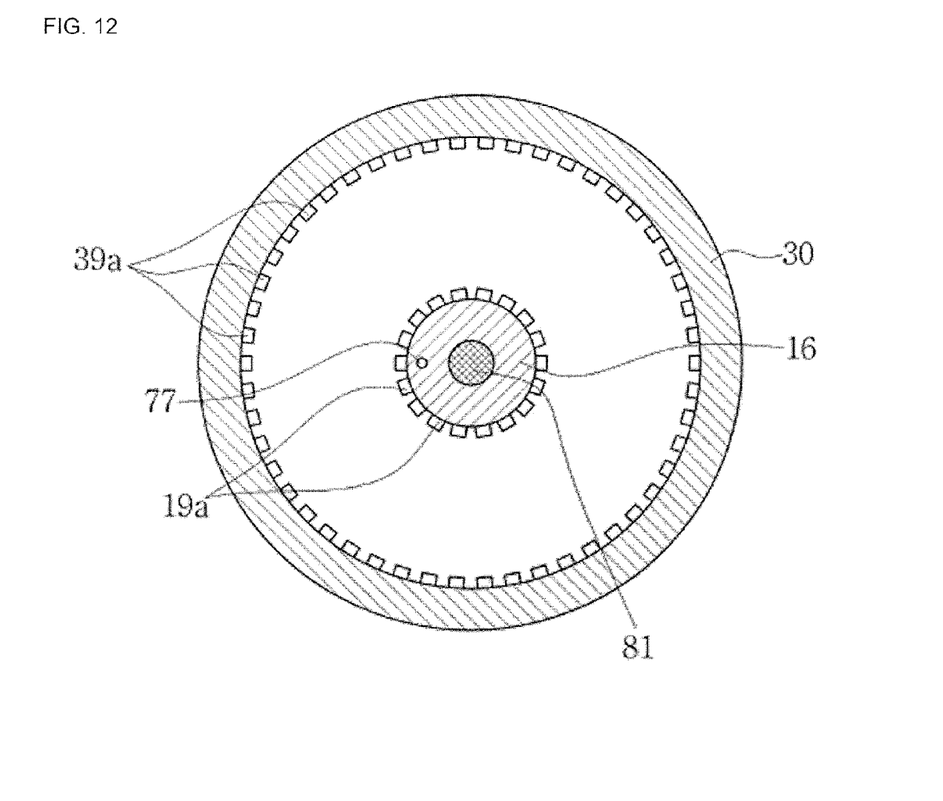
FIGS. 12 and 13 are views for explaining modified shapes of convex-concave portions.
Figure 13:
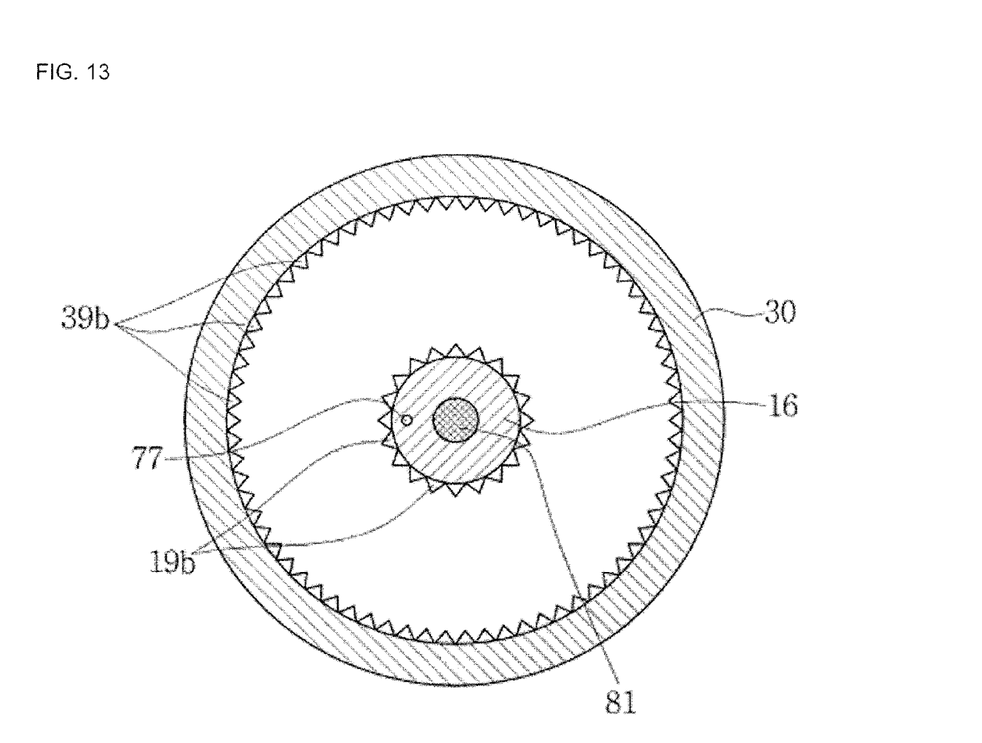

A cross-sectional shape of each of the protrusions 29, 39, and 19 formed on the upper ring 20, the lower ring 30, and the core 16 may be semi-circular or curved, as shown in FIG. 11; however, they may be formed as triangular or rectangular shapes, as shown in FIGS. 12 and 13. That is, the shape of each protrusion 29, 39, or 19 may be modified in various ways.

The upper ring 20 is pressurized toward the lower ring 30 due to a pressurization rod 81 and a driving portion 82 that will be described later, in order to prevent a gap between the upper ring 20 and the lower ring 30 from being formed when the upper ring 20 and the lower ring 30 are rotated relative to each other. The pressurization rod 81 and the driving portion 82 will be described later.

An O-ring 28 formed of rubber is interposed between a bottom surface of the upper ring 20 and a top surface of the lower ring 30 and performs a sealing function. Although not shown, when the upper ring 20 and the lower ring 30 are rotated relative to each other, the O-ring 28 may be rapidly worn out by friction. Thus, a friction reduction member (not shown) formed of metal and having a ring shape may be attached to a portion of the upper ring 20 and the lower ring 30 with which the O-ring 28 is not combined.

The load applying unit 40 is used to pressurize and to compact the soil samples accommodated in the first accommodation portion 21 and the second accommodation portion 31. A configuration of compacting the soil samples may be diverse, and a cylinder 45 and a pressurization plate 49 are used in the current embodiment.

The cylinder 45 includes a cylinder main body 41 that is installed at the upper plate 13 and operates by a pneumatic or hydraulic pressure, and a piston 42 combined with the cylinder main body 41 to make a reciprocating motion (vertical direction) as a pneumatic or hydraulic pressure is applied to the cylinder main body 41. An intermediate pin 43 is combined with a lower portion of the piston 42. A plurality of shafts 44 is disposed on a bottom surface of the intermediate plate 43 in the vertical direction. The plurality of shafts 44 is inserted in the upper ring 20 via a hole 24 formed in the cover 22, is combined with the pressurization plate 49, and transfers a pressure of the piston 45 to the pressurization plate 49. In the current embodiment, three shafts 44 are disposed at an angular interval of 120 degrees in order to transfer the pressure of the piston 45 to the pressurization plate 49 uniformly.

The pressurization plate 49 is formed in a ring shape to correspond to the first accommodation portion 21 and is disposed within the upper ring 20 with being inserted in the core 16. As the piston 42 ascends or descends, the pressurization plate 49 combined with the shafts 44 ascends together with the piston 42. When the piston 42 descends, the soil samples accommodated in the upper ring 20 and the lower ring 30 are pressurized and compacted, and when the piston 42 ascends, the compaction of the soil samples is released. The O-ring 48 is attached to outer and inner circumferential surfaces of the pressurization plate 49, respectively, prevents a gap between the upper ring 20 and the core 16 from being formed, and seals a space in which the soil samples are accommodated.

A rod cell 46 is disposed to measure pressure applied to the soil samples due to the cylinder 45. That is, the rod cell 46 is supported on an upper portion of the intermediate plate 43, and a lower end of the piston 42 is supported on a top surface of the rod cell 46. Thus, when the piston 42 is moved in a downward direction and pressurizes the soil samples, the pressure of the piston 42 is measured by the rod cell 46.

In addition, although not shown, a displacement sensor is disposed to measure displacement by which the soil samples are compacted by the piston 42. The displacement sensor does not measure compaction displacement of the soil samples but measures a distance at which the piston 42 is moved. Various types of displacement sensors may be used, and for example, an optical sensor may measure displacement of the piston 42 by using time when light is received or transmitted.

In the current embodiment, a load is applied to the soil samples due to the pressurization plate 49 in a range of 0.01 to 7.0 Kgf/cm$^2$, and maximum 50 mm of movement displacement of the piston 42 may be measured.

The rotating unit 50 is used to rotate the lower ring 30 and includes a rotating wheel 51, a driving gear 52, and a motor 53. The motor 53 is installed at the base plate 11, and the driving gear 52 having sawteeth formed on its outer circumferential surface is combined with a rotating shaft 54 of the motor 53.

The rotating wheel 51 is shaped as a ring, is inserted in the core 16, is combined with the lower portion of the lower ring 30, and is rotatably supported on the core 16 via a bearing 55. Sawteeth are formed on an outer circumferential surface of the rotating wheel 51 and are gear-coupled to the driving gear 52. A rotating force of the motor 53 is transferred to the lower ring 30 via the driving gear 52 and the rotating wheel 51 and allows the lower ring 30 to be rotated relative to the upper ring 20.

Since the motor 53 may adjust the number of rotations of the rotating unit 50, speed at which the soil samples are rotated, may be adjusted. In the current embodiment, the rotating unit 50 is rotated at an angular velocity of 0.03 to 10° per minute, and a rotating force loading stress is about 10 kN, maximum.

The shear strength measuring sensor 60 for measuring the shear strength of the soil samples is installed at the upper ring 20. In the current embodiment, the shear strength measuring sensor 60 is installed at both sides of the cover 22 fixed to the upper portion of the upper ring 20. In addition, the shear strength measuring sensor 60 is combined with the frame 14 and measures a shear strength (shear resistance) of the upper ring 20 that is generated due to rotation of the soil samples. The shear strength of the upper ring 20 may be measured in a range of a shear strain rate of $10^{-4}$ to 180 cm/sec.

When the lower ring 30 is rotated, a gap between the lower ring 30 and the upper ring 20 may be formed. Thus, the pressurization rod 81 and the driving portion 82 are disposed to pressurize the upper ring 20 toward the lower ring 30.

The pressurization rod 81 perforates the cover 22 and the core 16 while a head of the pressurization rod 81 is caught on the cover 22, and is inserted in a lower portion of the support plate 12. A lower end of the pressurization rod 81 is combined with the driving portion 82. The driving portion 82 may pull out the pressurization rod 81 in a downward direction by applying power to the pressurization rod 81. When the pressurization rod 81 is pressurized in the downward direction in this way, the head of the pressurization rod 81 pushes the cover 22 and the upper ring 20 in the downward direction so that the upper ring 20 is closely attached to the lower ring 30. The driving portion 82 may be a cylinder and may make a reciprocating motion by combining the pressurization rod 81 with a pinion by using a rack and the pinion. That is, various types of driving portions may be used.

According to the present invention, a water supply and drainage unit for supplying water to the soil samples in order to saturate the soil samples and for draining water from the soil samples is disposed in order to perform simulation of the landslip procedure similar to the reality. By using the water supply and drainage unit, the soil samples may be set on a saturation or unsaturation condition or a drainage or non-drainage condition.

The water supply and drainage unit includes a lower entrance path 71, a lower fluid path 72, and a porous plate 73. The porous plate 73 is disposed spaced apart from the bottom surface of the lower ring 30 by a predetermined distance in the upward direction, and the soil samples are put on the porous plate 73. The lower fluid path 72 on which a fluid flows, is formed between the porous plate 73 and the bottom surface of the lower ring 30. Since a plurality of through holes (not shown) is formed in the porous plate 73, the fluid that flows into the lower fluid path 72 may be supplied to the soil samples via the plurality of through holes. Alternatively, the fluid may be discharged from the soil samples to the lower fluid path 72. The lower entrance path 71 perforates sidewalls of the lower ring 30 and allows the lower fluid path 72 to communicate with the outside. A water supply and drainage line P via which the fluid is supplied or discharged, is connected to the lower entrance path 71.

Figure 9:
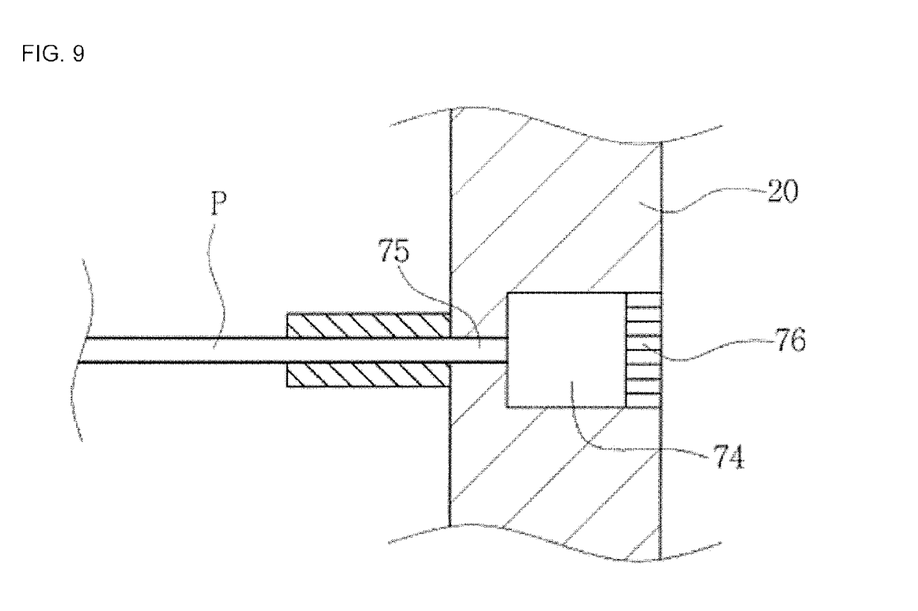
FIG. 9 is an enlarged view of portion A of FIG. 7.

In addition, the water supply and drainage unit includes an upper fluid path 74 and an upper entrance path 75. FIG. 9 is an enlarged view of portion A of FIG. 7. In FIG. 9, the upper fluid path 74 and the upper entrance path 75 are enlarged. Referring to FIG. 9, the upper fluid path 74 is concavely formed in a ring shape on sidewalls of the upper ring 30 along a circumferential direction of the upper ring 30. That is, a concave recess is formed on the sidewalls of the upper ring 30 along the circumferential direction of the upper ring 30, and a porous band 76 having a ring shape is attached to an exposed side of the recess. A space surrounded by the porous band 74 and the recess forms the upper fluid path 74. A plurality of holes is formed in the porous band 74 so that the fluid may flow via the plurality of holes. The porous band 74 is formed of metal and performs a function of a filter that filters water and does not filter soil particles. The upper entrance path 75 is formed on the sidewalls of the upper ring 20 and allows the upper fluid path 74 to communicate with the outside. Like the lower entrance path 71, a water supply and drainage line P is connected to the upper entrance path 75.

In addition, according to the present invention, a central fluid path 76 and a connection fluid path 77 are formed in the core 16 disposed in centers of the upper ring 20 and the lower ring 30. That is, like the upper fluid path 74, the central fluid path 76 is formed in such a way that a porous band 78 is installed at a recess formed as a ring shape along an outer surface of the core 16. The connection fluid path 77 perforates an inside of the core 16 and the cover 22 along a height direction of the core 16 and connects the central fluid path 76 and the water supply and drainage line P installed outside the upper ring 20.

A valve (not shown) is attached to a plurality of water supply and drainage lines P in order to adjust the amount of the fluid to be supplied or discharged. A gap water pressure measuring sensor (not shown) is combined with one of the plurality of water supply and drainage lines P connected to the upper entrance path 75 or the lower entrance path 71. That is, the gap water pressure measuring sensor measures a gap water pressure in the soil samples by measuring the water pressure of the fluid discharged from the soil samples.

In addition, according to the present invention, a controller (not shown), such as a computer, is disposed. Various measuring devices are connected to the controller and are controlled by the controller, and data measured by each measuring device is stored in the controller. That is, the rod cell 46 for measuring the pressure of the cylinder 45, the gap water pressure measuring sensor, the motor 53, and the like are connected to the controller, and data measured by each of the rod cell 46 for measuring the pressure of the cylinder 45, the gap water pressure measuring sensor, and the motor 53 is transmitted to the controller. Thus, when experiments are performed on various conditions, a condition value for each experiment and measured data are stored in the controller, which is advantageous to check the landslip procedure in a quantitative manner.

By using the ring shear apparatus 100 having the above structure, various conditions for the case where a shear strength of soil is measured while the landslip takes place may be implemented.

Basically, the lower ring 30 is rotated in the state where the soil samples are compacted by the load applying unit 40 so that the procedure of the landslip may be reproduced. The shear strength measuring sensor 60 combined with the upper ring 20 when the lower ring 30 is rotated, measures the shear strength of the soil samples. A load applied to soil may be adjusted, and a rotating speed of the lower ring 30 may be adjusted using a motor.

The soil samples may be fully or partially saturated by supplying water to the soil samples via the water supply and drainage line P. In addition, experiments may be performed on a condition that water in the soil samples is drained or not.

That is, a compaction (load) condition, a saturation/unsaturation condition, and a drainage/non-drainage condition in an actual natural environment are reproduced by using the ring shear apparatus so that the shear strength of soil in the procedure of the landslip may be checked in a quantitative manner.

In this way, the shear strength of soil in the procedure of the landslip is checked using the shear strength of soil by using the ring shear apparatus 100 illustrated in FIG. 1, thereby providing a database that predicts or prevents a landslip.

Figure 3:
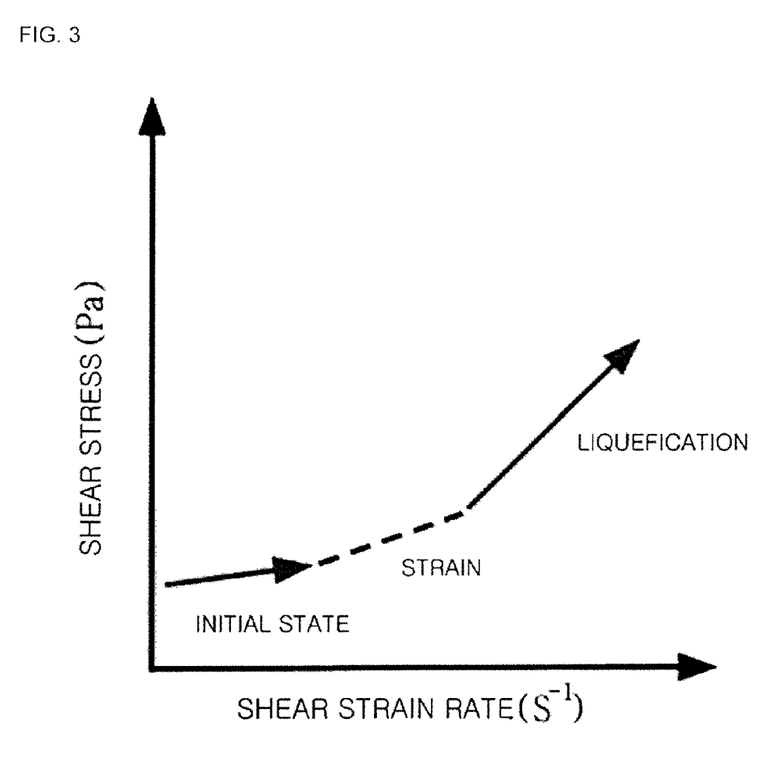
FIG. 3 is a graph showing the correlation between a shear stress and a shear strain rate while a landslip takes place and proceeds.
Figure 4:
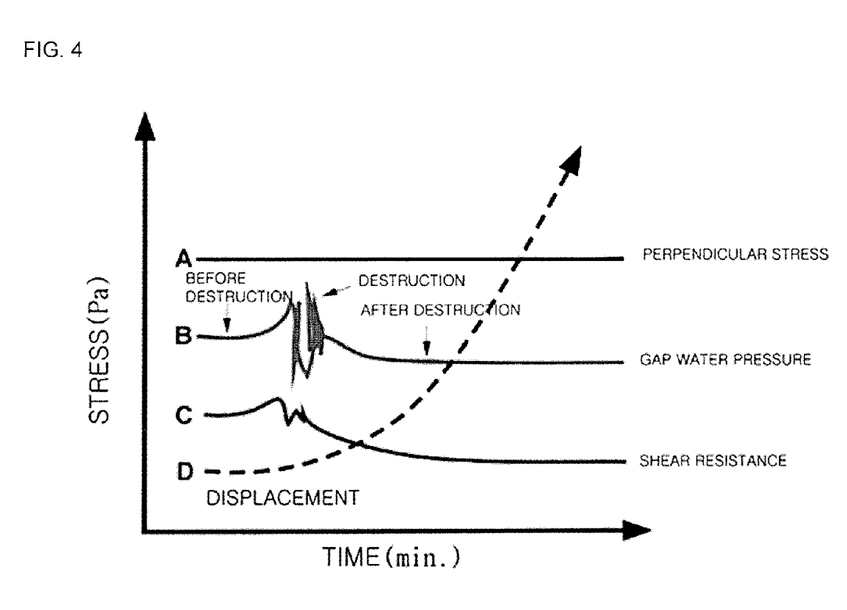
FIG. 4 is a graph showing a change of a shear stress in time-line when a landslip takes place.
Figure 5:
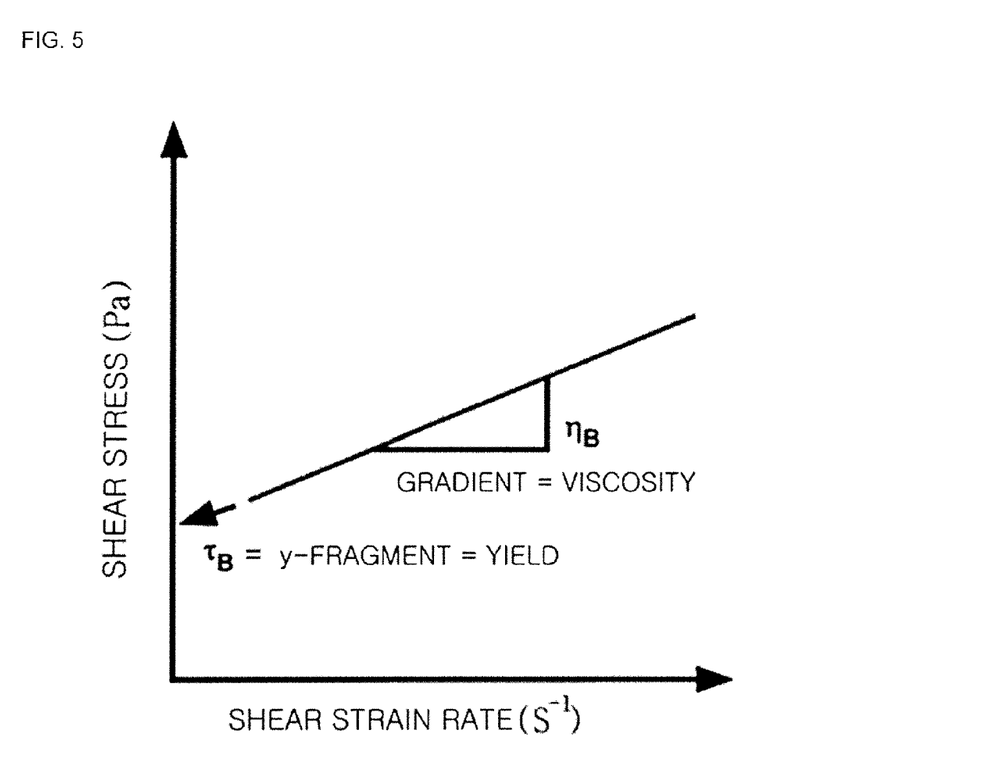
FIG. 5 is a graph showing the correlation between a shear stress and a shear strain rate of a debris flow while a landslip proceeds.

FIGS. 3 through 5 are graphs based on data obtained using the ring shear apparatus 100 illustrated in FIG. 1.

FIG. 3 is a graph showing the correlation between a shear stress and a shear strain rate while a landslip takes place and proceeds, FIG. 4 is a graph showing a change of a shear stress in time-line when a landslip takes place, and FIG. 5 is a graph showing the correlation between a shear stress and a shear strain rate of a debris flow while a landslip proceeds.

The graph of FIG. 3 shows a stage before a landslip takes place, and the movement of a progressive landslip that cannot be checked with naked eyes and moves very slowly may be explained by the relationship between the shear strain rate and the shear strength. The graph of FIG. 3 illustrates a process of liquefying a soil layer on the ground by fast re-forming (strain) after the soil layer on the ground loses its own resistance due to destructive causes.

The shear strength shows a very small change before a slope is destroyed, and a degree of the change is increased as it gets close to a destructive time. The slope reaches a destructive stage depending on a shear strength in a drainage and non-drainage state that is a base for determining destruction of the slope at a point of time when the landslip takes place and vanishment of a surplus gap water pressure corresponding to the shear strength.

FIG. 4 shows a rapid change of a shear strength due to an action of the surplus gap water pressure at the destructive time (A of FIG. 4) under a predetermined vertical stress (B and C of FIG. 4). Thus, after the landslip takes place, a strength function required to interpret the mobility of the landslip that moves like a debris flow quickly, may be presented.

After destruction, the surplus gap water pressure is vanished, and a shear resistance is rapidly reduced after the destructive time (B of FIG. 4). At this point of time, displacement of the soil mass proceeds rapidly (D of FIG. 4).

A yield stress and viscosity of a fluid corresponding to a residual stress may be obtained by analyzing rheology characteristics of the soil mass that is fully strained (re-formed) and liquefied (FIG. 5).

As described above, a ring shear apparatus according to the one or more embodiments of the present invention measures the shear strength of soil in quantitative manner on various conditions so that abundant data about the movement of the soil mass in the procedure of the landslip can be provided.

By using the ring shear apparatus according to the one or more embodiments of the present invention, a landslip in a dangerous area can be predicted or warned using accumulated data, and by connecting the ring shear apparatus to a landslip warning system, damage caused by the landslip can be prevented in advance.

In the ring shear apparatus according to the one or more embodiments of the present invention, convex protrusions are formed on inner wall surfaces of an upper ring and a lower ring in order to consider a wall-slip effect that, when the upper ring and the lower ring are rotated relative to each other, soil samples are slid on wall surfaces of the upper ring and the lower ring, so that a shear strength of soil can be very precisely measured.

In addition, since saturation or unsaturation, drainage or non-drainage, and compaction conditions are freely adjusted, the movement of soil, in particular, the shear strength of soil can be measured while a landslip takes place by setting various conditions, and measured data can be made as a database and can be utilized as basic data for research on landslips.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A ring shear apparatus comprising:
an upper ring for forming a first accommodation portion having a ring shape in which soil samples are accommodated;
a lower ring for forming a second accommodation portion that corresponds to the first accommodation portion of the upper ring and that has a ring shape in which soil samples are accommodated, closely attached to a lower portion of the upper ring and rotatably installed relative to the upper ring;
a rotating unit for rotating the lower ring relative to the upper ring; and
a shear strength measuring sensor combined with the upper ring and for measuring a shear strength of the soil samples,
wherein a plurality of protrusions that protrudes from the lower ring is formed on an inner circumferential surface of the lower ring along a circumferential direction of the lower ring in order to prevent the soil samples from being slid when the lower ring is rotated.

2. The ring shear apparatus of claim 1, further comprising a core having a cylindrical shape and installed fixedly,
wherein the upper ring is inserted in the core and is fixed to the core, and the first accommodation portion is formed by the upper ring and the core, and the lower ring is rotatably inserted in the core, and the second accommodation portion is formed by the lower ring and the core, and a plurality of protrusion that protrudes from the core is formed on an outer circumferential surface of the core along a circumferential direction of the core.

3. The ring shear apparatus of claim 1, wherein a plurality of protrusions that protrudes from is formed on an inner circumferential surface of the upper ring along a circumferential direction of the upper ring.

4. The ring shear apparatus of one of claim 1, wherein the plurality of protrusions has one cross-sectional shape selected from the group consisting of a semi-circular shape, a triangular shape, and a rectangular shape.

5. The ring shear apparatus of claim 1, wherein convex portions are formed on a support surface of the lower ring for supporting the soil samples and a top surface of the upper ring and are disposed in a radial shape.

6. The ring shear apparatus of claim 1, further comprising:

a load applying unit for applying a load to the soil samples accommodated in the first accommodation portion and the second accommodation portion; and a water supply and drainage unit for supplying water to the soil samples accommodated in the first accommodation portion and the second accommodation portion and for draining or for not draining water in the first accommodation portion and the second accommodation portion selectively.

7. The ring shear apparatus of claim 6, further comprising a cover combined with an upper portion of the upper ring to be attached to or detached from the upper ring and for sealing the first accommodation portion, wherein the load applying unit comprises:

a cylinder comprising a cylinder main body and a piston installed to be slidable on the cylinder main body; and a pressurization plate having a ring shape, connected to the piston, disposed on a lower portion of the cover and for pressurizing the soil samples accommodated in the first accommodation portion.

8. The ring shear apparatus of claim 7, wherein the load applying unit comprises:

an intermediate plate installed at a lower portion of the piston;

a rod cell installed between the intermediate plate and the lower portion of the piston and for measuring a load of the piston; and a plurality of shafts perforating the cover from a bottom surface of the intermediate plate, combined with the pressurization plate, transferring a load of the piston to the pressurization plate, and spaced apart from each other by the same angular interval.

9. The ring shear apparatus of claim 6, wherein the water supply and drainage unit comprises:

a porous plate spaced from the bottom surface of the lower ring by a predetermined distance in an upward direction, supporting the soil samples, and having a plurality of holes formed in the porous plate;

a lower fluid path formed between the porous plate and the bottom surface of the lower ring;

a lower entrance path perforating the lower ring to communicate with the lower fluid path;

an upper fluid path formed in a ring shape along an inside of the upper ring; and an upper entrance path perforating the upper ring to communicate with the upper fluid path.

10. The ring shear apparatus of claim 9, wherein the water supply and drainage unit further comprises a gap water pressure measuring sensor combined with a water supply and drainage line connected to the lower entrance path or the upper entrance path and for measuring a gap water pressure in the soil samples.

11. The ring shear apparatus of claim 1, wherein the rotating unit comprises:

a driving gear having sawteeth formed on an outer circumferential surface of the driving gear;

a motor connected to the driving gear and for rotating the driving gear; and a rotating wheel having sawteeth formed on an outer circumferential surface of the driving gear, gear-coupled to the driving gear, receiving a rotating force of the motor, and combined with the lower ring.

12. The ring shear apparatus of claim 6, further comprising a displacement sensor for measuring displacement at which the soil samples are compacted, by using the load applying unit.

* * * * *